(12) United States Patent
Myles

(10) Patent No.: US 7,150,714 B2
(45) Date of Patent: Dec. 19, 2006

(54) MINIMALLY INVASIVE SURGICAL SPINAL EXPOSURE SYSTEM

(75) Inventor: Robert T. Myles, Colleyville, TX (US)

(73) Assignee: EBI, L.P., Parsippany, NJ (US)

( * ) Notice: Subject to any disclaimer, the term of this patent is extended or adjusted under 35 U.S.C. 154(b) by 184 days.

(21) Appl. No.: 10/867,354

(22) Filed: Jun. 14, 2004

(65) Prior Publication Data

US 2005/0277812 A1 Dec. 15, 2005

(51) Int. Cl.
*A61B 1/32* (2006.01)
(52) U.S. Cl. .................... 600/205; 600/223; 600/219
(58) Field of Classification Search ............. 600/224, 600/211, 223, 245, 210, 215, 212
See application file for complete search history.

(56) References Cited

U.S. PATENT DOCUMENTS

| | | | |
|---|---|---|---|
| 475,975 A | 5/1892 | Clough | |
| 497,064 A | 5/1893 | Van Meter | |
| 1,157,202 A | 10/1915 | Bates et al. | |
| 1,246,338 A | 11/1917 | Smit | |
| 3,626,471 A | 12/1971 | Florin | 128/20 |
| 3,965,890 A | 6/1976 | Gauthier | 128/20 |
| 4,156,424 A | 5/1979 | Burgin | 128/18 |
| 4,263,899 A | 4/1981 | Burgin | 128/18 |
| 4,300,541 A | 11/1981 | Burgin | 128/18 |
| 4,562,832 A * | 1/1986 | Wilder et al. | 600/223 |
| 4,867,141 A * | 9/1989 | Nakada et al. | 601/4 |
| 4,926,849 A | 5/1990 | Downey | |
| 5,512,038 A | 4/1996 | O'Neal et al. | |
| 5,520,611 A | 5/1996 | Rao et al. | 600/245 |
| 5,616,117 A | 4/1997 | Dinkler et al. | |
| 5,728,046 A | 3/1998 | Mayer et al. | 600/210 |
| 5,755,660 A * | 5/1998 | Tyagi | 600/205 |
| 5,785,648 A * | 7/1998 | Min | 600/206 |
| 5,795,291 A | 8/1998 | Koros et al. | |
| 5,813,978 A * | 9/1998 | Jako | 600/201 |
| 5,882,298 A | 3/1999 | Sharratt | |
| 5,908,382 A | 6/1999 | Koros et al. | |
| 5,928,139 A * | 7/1999 | Koros et al. | 600/205 |
| 5,944,658 A | 8/1999 | Koros et al. | |
| D415,274 S | 10/1999 | Koros et al. | |
| 5,993,385 A | 11/1999 | Johnston et al. | |
| 6,139,493 A * | 10/2000 | Koros et al. | 600/215 |
| 6,185,356 B1 | 2/2001 | Parker et al. | 385/133 |
| 6,224,545 B1 | 5/2001 | Cocchia et al. | 600/233 |
| 6,416,467 B1 | 7/2002 | McMillin et al. | |
| 6,464,634 B1 | 10/2002 | Fraser | 600/233 |
| 6,504,985 B1 | 1/2003 | Parker et al. | 385/133 |
| 6,616,605 B1 | 9/2003 | Wright et al. | |

(Continued)

*Primary Examiner*—Cary E. O'Connor
(74) *Attorney, Agent, or Firm*—Harness, Dickey & Pierce, P.L.C.

(57) ABSTRACT

A minimally invasive retractor system is shown which has a support frame having two opposing pairs of horizontally oriented sides. The sides of the frame can be adjusted to vary an interior space of the frame. Four retractor blades are mounted on the frame for engaging tissue within a surgical site. Each retractor blade has an elongate body portion with a length which is oriented perpendicularly to the frame in use. One of the retractor blades can be equipped with a light source and a suction source which are integral to the blade. The blade also has an integral power source for powering the light source. The blade can also house a tissue retractor such as a dural retractor for retracting the dural sack of a patient during spinal surgery.

15 Claims, 6 Drawing Sheets

U.S. PATENT DOCUMENTS

| | | |
|---|---|---|
| 6,712,795 B1 | 3/2004 | Cohen |
| 6,869,398 B1 | 3/2005 | Obenchain et al. |
| 6,945,933 B1 | 9/2005 | Branch et al. |
| 2003/0095781 A1 | 5/2003 | Williams .................... 385/146 |
| 2004/0087833 A1 | 5/2004 | Bauer et al. ................ 600/201 |
| 2004/0215199 A1 | 10/2004 | Zinkel |

* cited by examiner

MINIMALLY INVASIVE SURGICAL SPINAL EXPOSURE SYSTEM

BACKGROUND OF THE INVENTION

A. Field of the Invention

The present invention relates generally to the field of minimally invasive surgical instruments, and more particularly, to a visual blade retractor system which will allow greater access and visual exposure in the surgical area, along with improved instrument control, orientation and versatility.

B. Description of the Prior Art

Minimally invasive surgical techniques have become increasingly popular due to the rapid healing and greater efficiency provided by such techniques. As these techniques have been developed, workers and surgeons have been faced with the problem of working in small places not visible by direct line of sight. Various tools have been designed to deal with this problem although none has been entirely satisfactory.

The standard surgical approach has been to make a large enough opening in an anatomically suitable location (which will heal without functional impairment) to establish direct visualization. Magnification can then be used to enlarge the target structure and various fiberoptic light or scope delivery systems can be used to illuminate it. The actual surgical manipulation is then performed by direct manipulation of instruments held in the surgeons' hands. Even with the advent of minimally invasive surgical techniques, many surgical procedures still require an exposed surgical field for the surgeon to successfully perform. Often, the greater the visibility and access a surgeon has to a surgical site, the greater the probability that a successful outcome will result. Once entry is made into a patient, soft tissue is dissected away further exposing the field. However, the exposed field must be maintained using instruments that do not obstruct either visual or physical access. Surgical retractors are used to maintain exposure and access to a surgical field. There are a variety of retractors, and different surgical protocols require different styles of retractors. For example, in lumbar surgery the retractor needs to be strong enough to overcome the force exerted by the large muscle mass that has been dissected away from the field of exposure, while maintaining a visual field and access by the surgeon. Additionally, retractors are often required to partition other soft-tissue components of the surgical field.

One example of the need for improvements in minimally invasive surgery is in the area of minimally invasive spinal surgery. Modern spinal surgical techniques, for example, often call for the implantation of fusion devices into the disc space. These methods include anterior, lateral, posterolateral and posterior approaches to the subject disc space. Many traditional surgical procedures for correction of disc space pathologies can cause significant trauma to the intervening tissues. These open procedures often require a long incision, extensive muscle stripping, prolonged retraction of tissues, denervation and devascularization of tissue. Most of these surgeries require significant post-operative recovery time due in part to the necessary destruction of tissue during the surgical procedure. Minimally invasive surgical techniques are particularly desirable for spinal and neurosurgical applications because of the need for access to locations deep within the body and the danger of damage to vital intervening tissues. The development of minimally invasive spinal procedures has yielded a major improvement in reducing recovery time and post-operative pain because they require minimal, if any, muscle dissection and they can be performed under local anesthesia. However, one drawback associated with minimally invasive procedures is the relatively small amount of working space available to the surgeon adjacent the cannula or sleeve providing access to the surgical site. Minimally invasive spinal surgery is the future of spinal surgery. However, there are few new minimally invasive systems on the market, all in the infancy in their design. Most of the existing systems are crude in respect to the demands required by a minimally invasive spinal surgeon. Limitations of these new minimally invasive systems include inadequate lighting, limited visualization, poor surgical site access, cumbersome instrument access, poor retraction of deep tissue and crowding of instruments into the portal.

A need exists, therefore, for an improved minimally invasive system which will eliminate the above type limiting factors of the presently existing instruments on the market.

A need also exists for a system which will provide greater flexibility in a surgical retractor system while improving both visual and physical access by the surgeon to the surgical field. In the case of spinal surgery, a need exists for such improved instruments and techniques which will provide for safe and effective disc space preparation and implant insertion while minimizing trauma to tissue surrounding the surgical site.

SUMMARY OF THE INVENTION

The minimally invasive surgical fixation system of the invention will eliminate many of the previously discussed limiting factors of the presently existing systems. A surgeon who prefers direct visualization by looking down the surgical portal, or the surgeon who prefers indirect visualization with a scope can use this new system. The new system concept of the invention will offer superior lighting and visualization when compared to the systems presently on the market. The improved lighting and visualization is created by incorporation of the light source, a light power source, the scope, a suction device and a dural retractor, or selected ones of these devices into a retraction blade. These features eliminate cords and cannulas from the portal visual site, thereby increasing the area in the visual field. A larger visual field increases the surgeon's ability to identify anatomy and operate with correct surgical orientation.

Placement of the light source in the retraction blade allows light to be focused only in the surgical site. This eliminates glare caused when over head lights or a head light beam hits a shiny retractor. Since the light and power source is very close to the surgical site, only small amounts of light energy will be required for a powerful lighting effect. Placement of the light source in the blade allows lower wattage lighting, which is safer for the patient.

The system of the invention utilizes four blades in the preferred retractor system. This allows the ability to place space between the blades, which allows variable angles of instrument access through the portal. The four independent blades easily allow the width of this portal to be adjusted by the surgeon according to the needs required for the surgical procedure.

Because of the versatility offered by this new system, if necessary, the surgeon can quickly convert the surgical procedure from a minimally invasive case to an open case by simply changing the position of the blades. It is not necessary to remove the minimally invasive access apparatus and replace it with open system retractors. There are numerous other advantages of the present system which will become apparent in the written description which follows.

In one particularly preferred embodiment of the invention, the minimally invasive surgical exposure system includes a support frame having opposing horizontally oriented sides, the sides being arranged to lie in a common plane generally perpendicular to one another in use, at least selected ones of the sides of the support frame being provide with holding fixtures for engaging a retractor blade. At least one retractor blade having a fastening element is engageable with a selected holding fixture of the support frame. The retractor blade has a substantially elongate, planar body portion having a length which extends in a plane generally perpendicular to the plane of the support frame when in use. The planar body portion of the retractor blade has incorporated therein at least one visualization channel including an upper extent and a lower extent, the lower extent being located proximate a site within a surgical portal when in use. A light source is incorporated integrally with the blade, the light source being located in communication with the visualization channel for illuminating the site. A power source is also incorporated integrally with the blade for powering the light source.

Preferably, the planar body portion of the retractor blade is also provided with an elongate utility channel which extends from an upper extent of the blade to a lower extent thereof, the utility channel housing a selectable utility device which is used during surgery. In one embodiment of the invention, the selectable utility device is a suction device having an upper end and a lower end, the lower end being dispatchable from the blade lower extent into the surgical site. The suction lower end preferably has incorporated therein a coiled wire which can be controlled through tension to allow desired placement into the surgical site.

The elongate body portion of the retractor blade can also house a tissue retractor. The tissue retractor has a first section coplanar with the elongate body portion of the blade and a second section angularly oriented with respect to the first section for engaging tissue within a surgical site. The tissue retractor is slidably received within an elongate passage substantially centrally formed in the elongate body portion of the blade. The tissue retractor can comprise a dural retractor for retraction of a dural sack in the spinal canal of a patient undergoing spinal surgery. Additional objects, features and advantages will be apparent in the written description which follows.

DETAILED DESCRIPTION OF THE INVENTION

Figure 1:
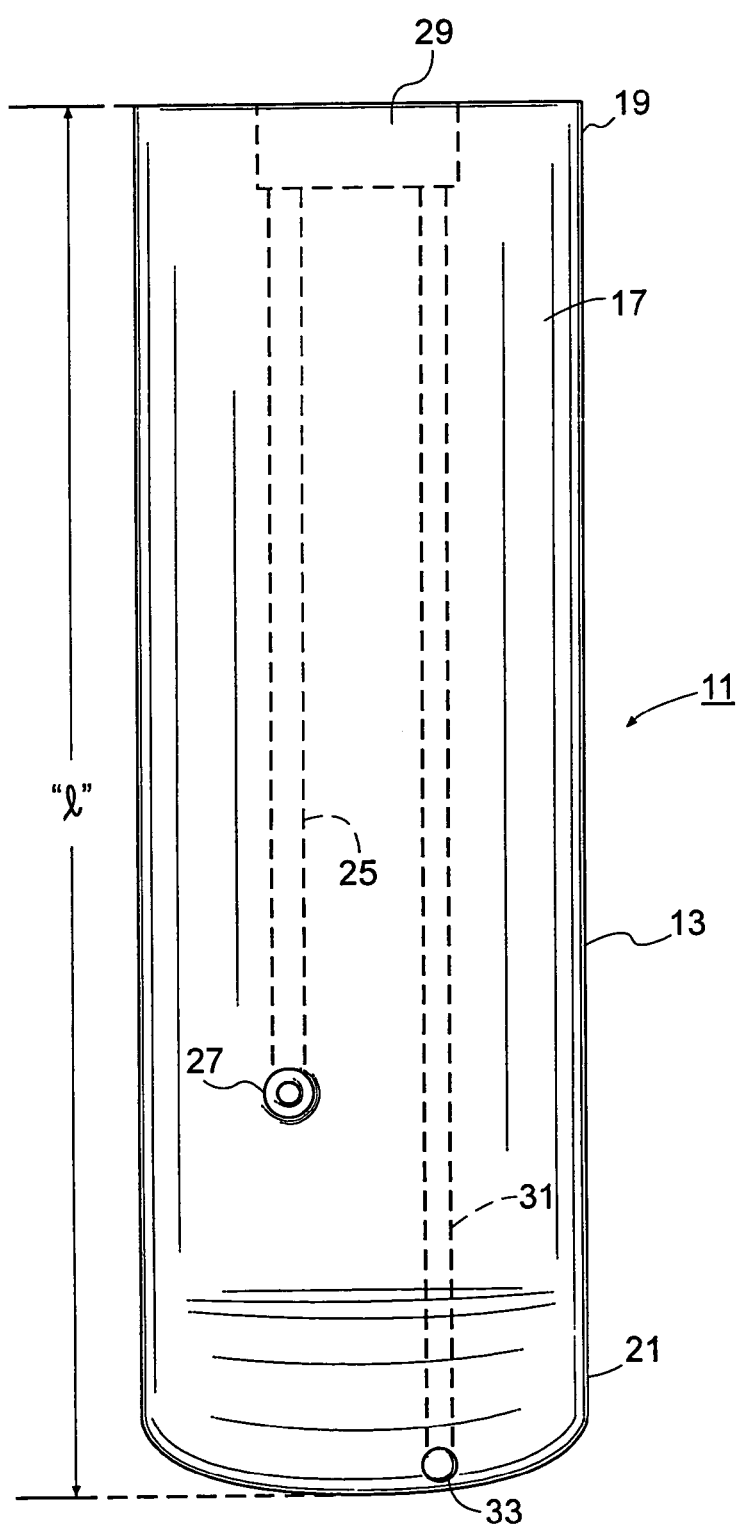
FIG. 1 is a planar view of an inner surface of a retractor blade of the invention showing the visualization channel and the utility channel thereof in dotted lines.
Figure 2:
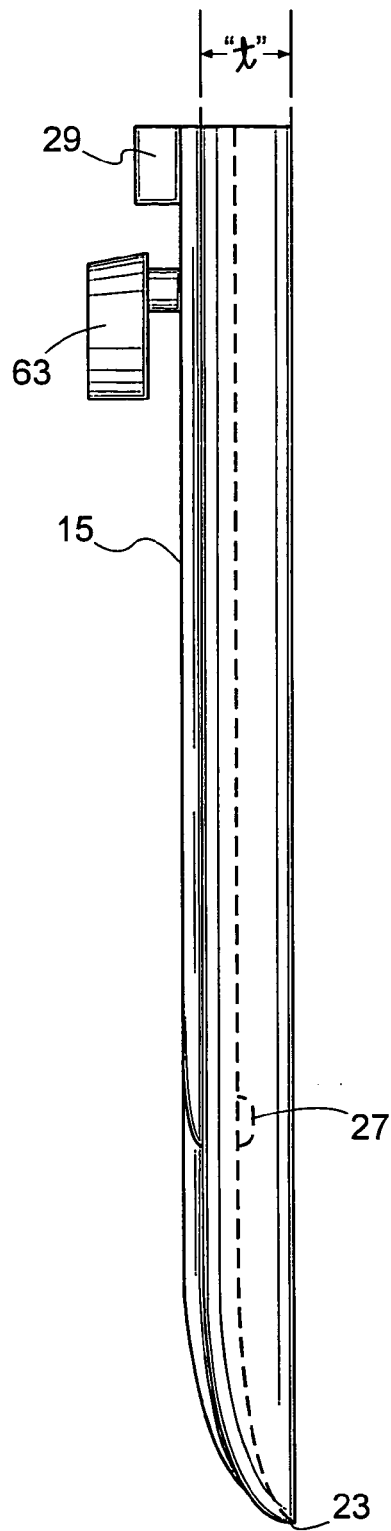
FIG. 2 is a side view of the retractor blade of FIG. 1.
Figure 3:
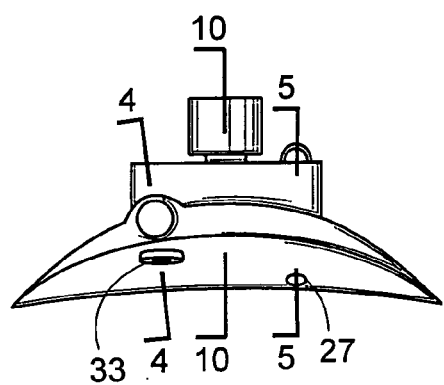
FIG. 3 is a top view of the retractor blade of FIG. 1.
Figure 4:
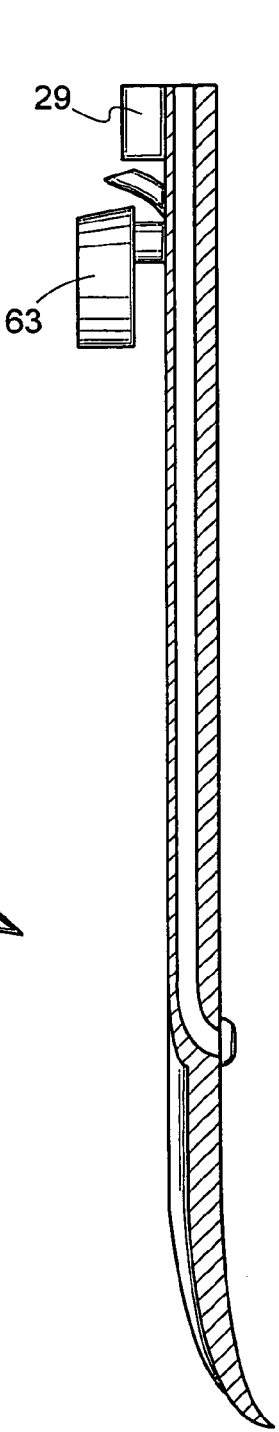
FIG. 4 is a sectional view of the retractor blade of Figure one showing the visualization channel.

Turning to FIG. 1, there is shown a retractor blade 11 of the type used in the practice of the present invention. The retractor blade 11 has a substantially elongate, planar body portion 13 having a length "1" and having a thickness ("t" in FIG. 2). The body portion 13 is also defined by an outer planar surface 15 and an inner planar surface 17. As best seen in FIG. 2, the body portion is generally uniform in thickness along the width thereof but tapers from an upper extent 19 as it approaches a lower extent 21, terminating in a tip region 23.

The elongate body portion 13 of the retractor blade has incorporated therein at least one visualization channel 25 which, in the embodiment of FIG. 1, runs from the upper extent 19 down about ⅘ of the length of the blade. The visualization channel 25 is used to house a light source which is integral with the blade itself. For example, the light source could be a light bulb 27 which is connected by electrical wires running up the channel 25 to a suitable power source, such as the battery pack 29 which is carried on the exterior of the blade body portion. Alternatively, the light source might be a bulb or other type light source located in the upper extent of the blade having an associated fiber optic strand or cable which leads to a digital light hole (which could also be represented by the object 27 in FIG. 1). Again, the light source would be powered by the battery pack 29.

The visualization channel might also be used to house a camera or a scope such as an endoscopic instrument of the type used in a specific surgical procedure. In this way, a surgeon who prefers direct visualization by looking down the portal, or the surgeon who prefers indirect visualization with a scope can use the system of the invention. As mentioned in the background discussion, the system of the invention offers superior lighting and visualization when compared to systems presently on the market by incorporation of the light, the scope, or additional utility device integrally into the retractor blade. The integral battery pack also eliminates the need for cords and cannulas from the portal visual site, thereby increasing the area in the visual field. A larger visual field increases the surgeon's ability to identify anatomy and operate with correct surgical orientation.

Figure 5:
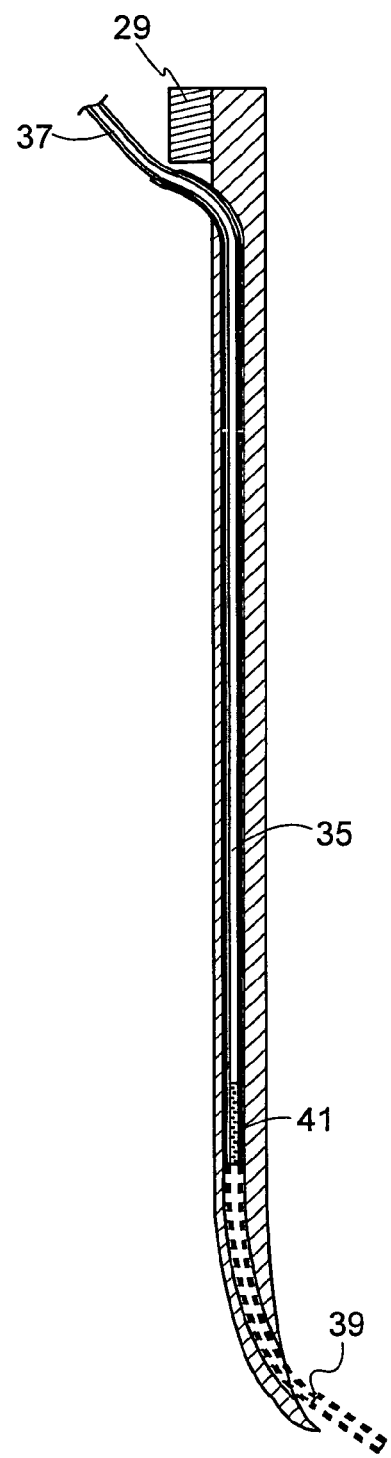
FIG. 5 is another sectional view of the blade of FIG. 1, showing the utility channel housing a suction device.

As briefly mentioned, the body portion 13 of the retractor blade may also include an elongate utility channel 31 which extends from the upper extent 19 of the blade substantially along the entire length "1" to the lower extent 21, thereof. In the embodiment of the invention illustrated in FIG. 2, the utility channel 31 terminates in an end opening 33. The utility channel 31 houses a selected utility device which is used during surgery. For example, the channel 31 in FIG. 5 houses a suction device 35. The suction device 35 has an upper end 37 and a lower end 39 which is dispatchable from the end opening 33 in the blade lower extent 21 into the surgical site. Preferably, the suction device 35 has incorporated therein a coiled wire 41 which acts as a spring and which can be controlled by the surgeon through tension on the upper, exposed end 37 to allow a desired placement of the suction device into the surgical site.

Figure 8:
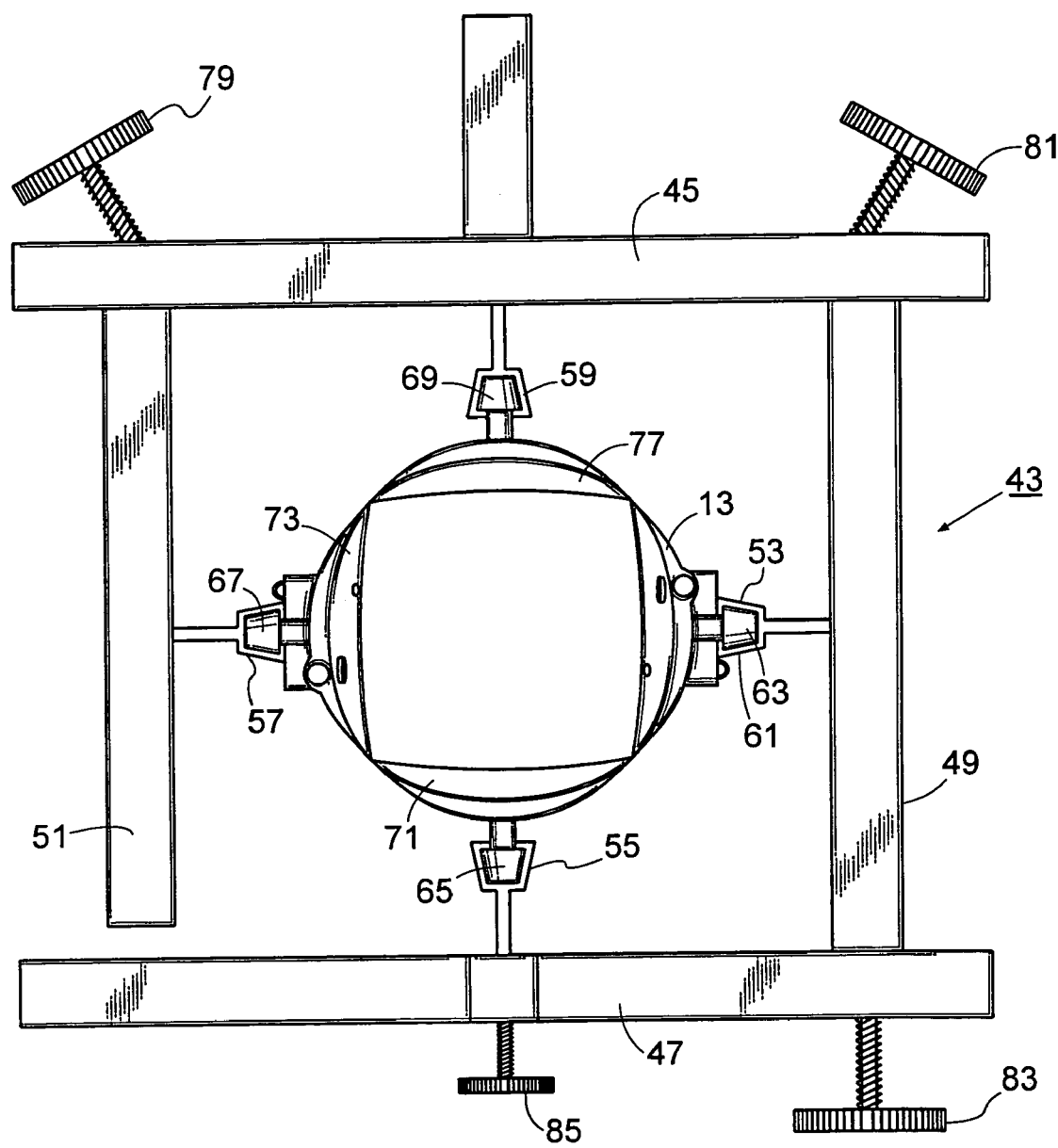
FIG. 8 is an isolated top view of the retractor system of the invention.

Turning now to FIG. 8, there is shown a support frame for use with the retractor blade system of the invention, designated generally as 43. The support frame 43 has opposing horizontally oriented sides 45, 47 and 49, 51, respectively, the sides being arranged to lie in a common plane generally perpendicular to one another in use. In other words, sides 49, 51 are arranged generally perpendicular to sides 45, 47, in use. At least selected ones of the sides 45, 47, 49, 51 are provided with holding fixtures for engaging a retractor blade. In the preferred embodiment of the invention shown in FIG. 8, each side of the frame 43 has a holding fixture, designated as 53, 55, 57, 59. The holding fixtures can be as simple as flanges having internal channels, e.g., channel 61, for receiving mating flanges 63, 65, 67, 69 provided on the outer planar surface 15 of the retractor blade (see FIG. 2). The channel 61 and mating flange 63 form a wedge-shaped interfit in the particular embodiment of the invention illustrated.

When the blades (designed as 13, 71, 73, 75 in FIG. 8) are arranged in the support frame 43, the planar body portions thereof have a length which extends in a plane generally perpendicular to the plane of the support frame. The preferred support frame 43 comprises a four sided, substantially square member having an open interior space which is adjustable for engaging patient tissue. As will be explained in greater detail, the support frame 43 is used for spreading open an incision in the patient's tissue in substantially a first plane, to create a surgical portal and wherein at least selected sides of the support frame are mechanically coupled together for adjusting the interior space between the sides of the support frame. In the embodiment of the invention illustrated in FIG. 8, the sides of the support frame 43 are coupled together by means of a gear system including adjustment knobs 79, 81, 83, 85. The knobs 79 and 81 are used to move sides 49 and 51 in and out in a sidewise lateral direction, as viewed in FIG. 8. The knob 83 is used to move side 47 up and down as viewed in FIG. 8. Knob 85 is a fine adjustment control which is used to determine the exact final position of flange 55.

Figure 6:
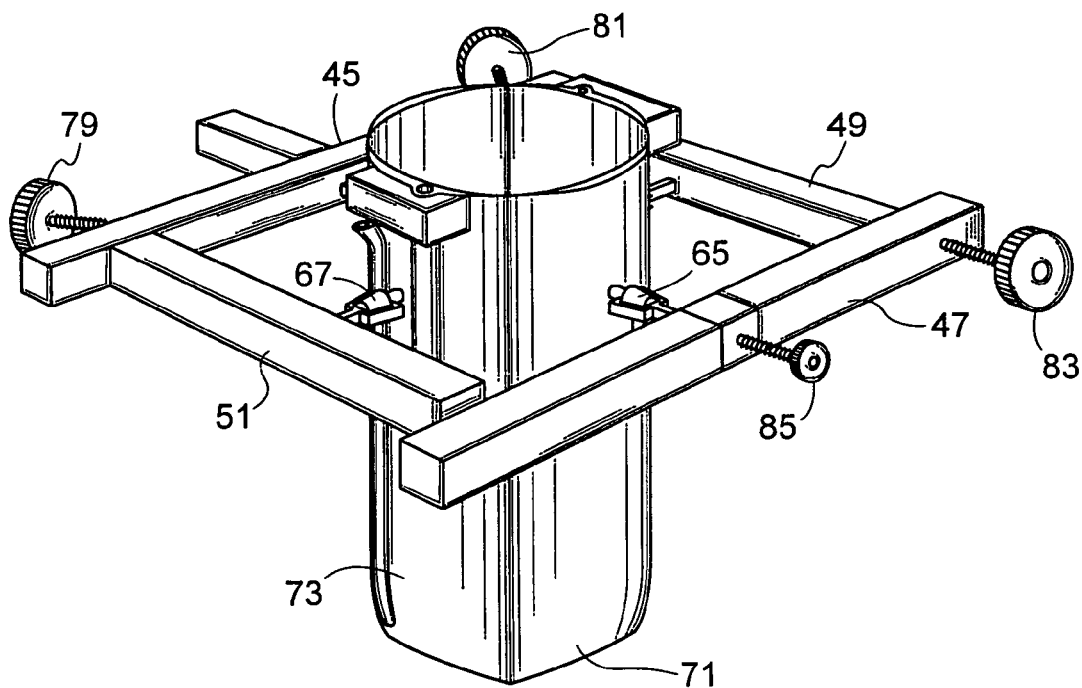
FIGS. 6 and 7 are perspective views of the support frame and retractor blades which make up the minimally invasive fixation system of the invention with the blades in the fully extended position.
Figure 7:
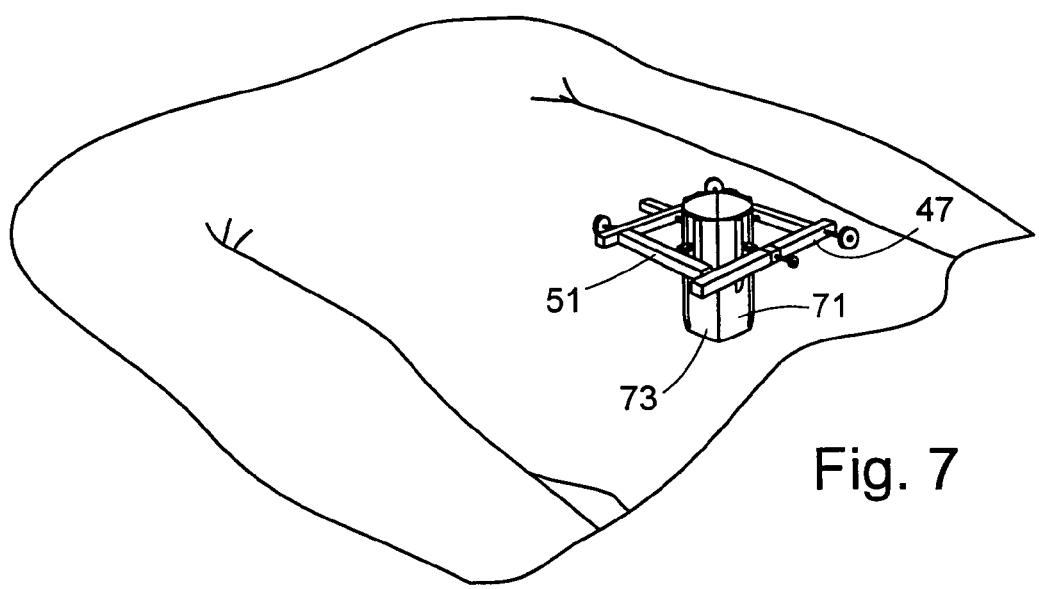

FIGS. 6 and 7 show the support frame and associated retractor blades in place on the spinal region of a patient undergoing a spinal procedure. A typical procedure would involve the following general steps:

1. Portal Placement: A stab wound is created over the radio logically verified intervertebral site. A long spinal needle or guide wire is placed through the stab incision and docked on the inferior portion of the upper vertebral lamina. Placement of the guide wire is verified using a C arm.

2. Skin Incision: The incision in the skin is lengthened in the caudal-chephalad direction. Then a T type shaped incision is made in the fascia, around the guide wire.

3. Dilator Placement: Dilators are placed over the guide wire and continued sequentially until the last dilator is placed.

4. Blade Placement: The four blades 13, 71, 73, 77 including the visual blade 13 are placed over the last dilator. The support frame 43 is slid over the blade ends and each blade is docked onto the support frame by engaging the respective flange channels and mating blade flanges (e.g., 55, 65). The dilators are then removed. Then each blade is distracted independently until the desired portal width is established in the patient tissue. Each blade is then locked in the desired position by means of the adjustment knobs 79, 81, 83, 85.

5. Light Connection: Once the blades are fixed in position, the connections between the light/camera and/or suction are accomplished.

Figure 9:
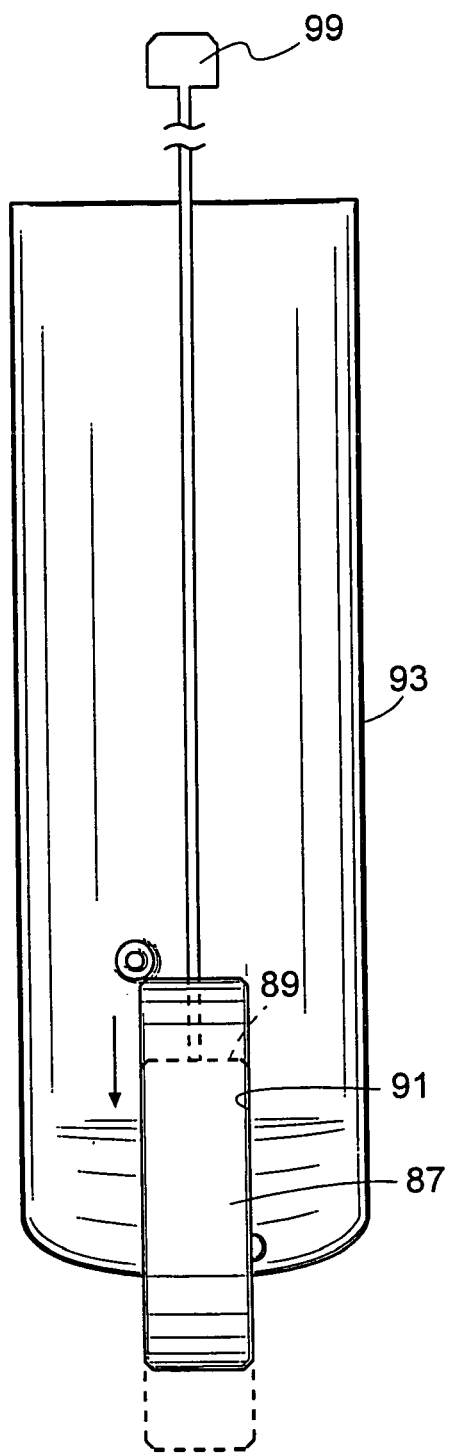
FIG. 9 is plan view of another version of the retractor blade of the invention, showing a tissue retractor incorporated into the retractor blade.
Figure 10:
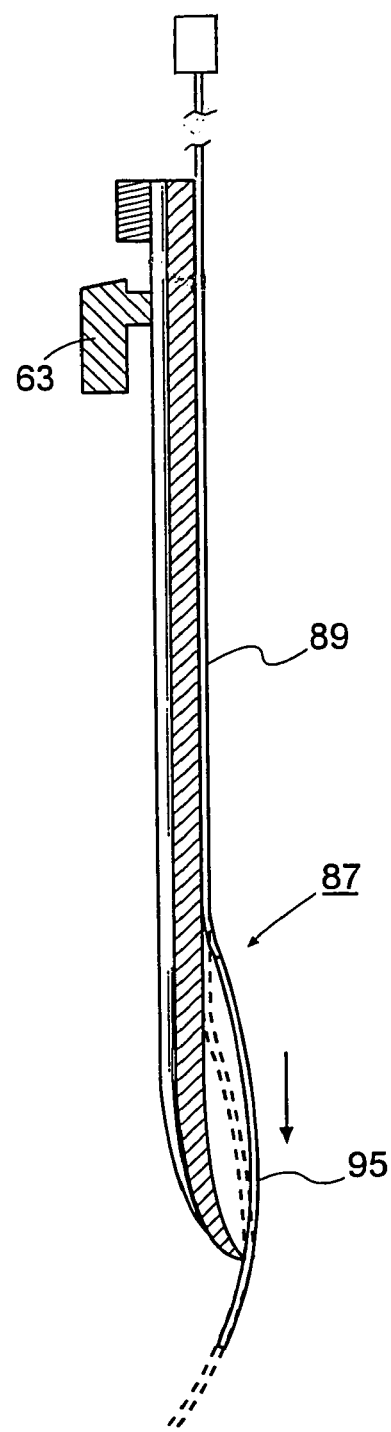
FIG. 10 is a side view of the retractor blade of FIG. 9, showing further details of the tissue retractor.
Figure 11:
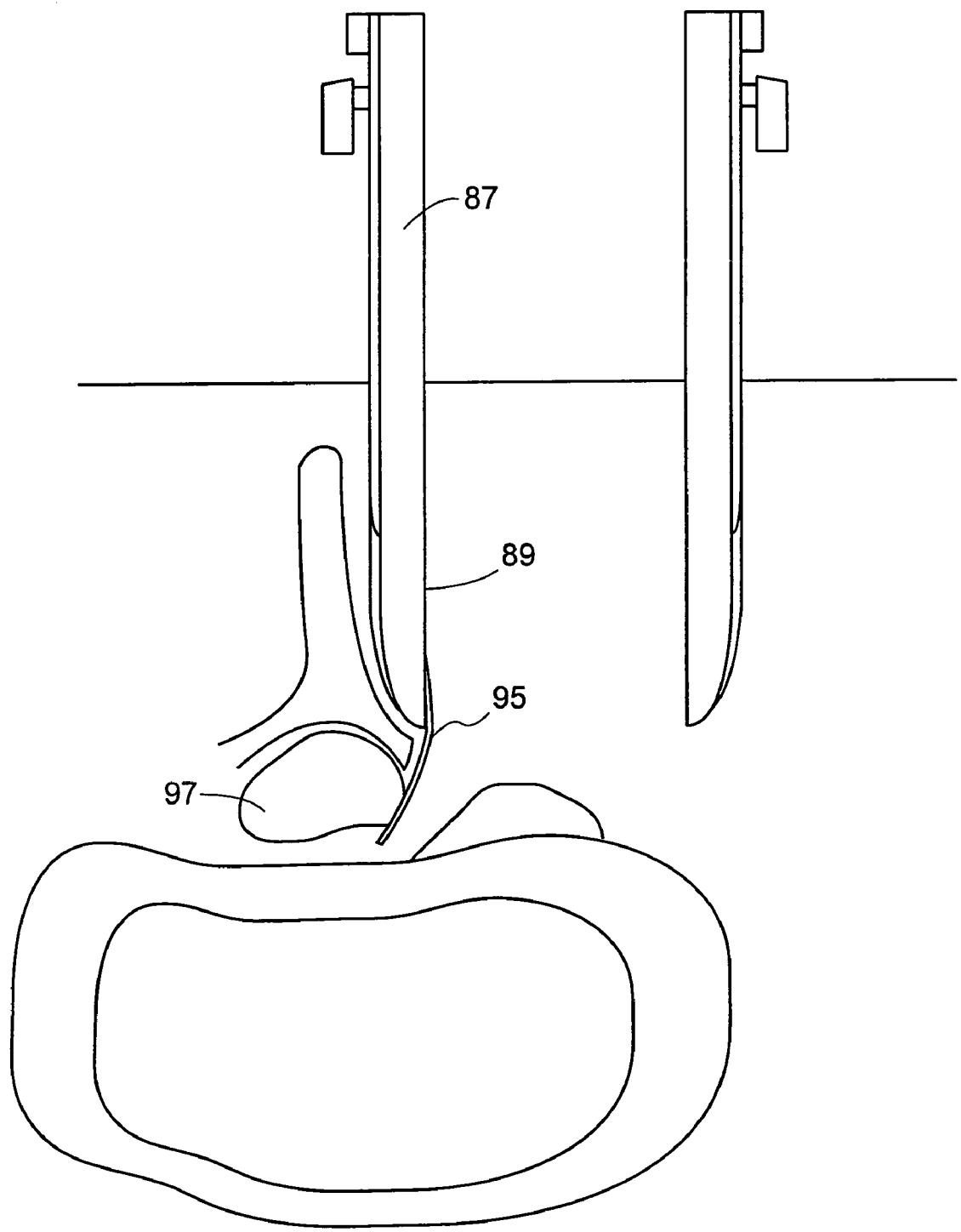
FIG. 11 is a simplified, partially schematic view of the retractor blade of FIG. 9 being used to engage the dural sack of a patient.

Turning to FIGS. 9–11, there is shown an additional version of the retractor blade of the invention in which the elongate body portion of the blade also houses a tissue retractor 87. The tissue retractor has a first section 89 coplanar with the elongate body portion which is slidably received within an elongate passageway 91 substantially centrally located in the elongate body portion of the retractor blade 93. The tissue retractor also has a second section 95 which extends outwardly from the body portion of the blade and which is angularly oriented with respect to the first section for engaging tissue within a surgical site. With respect to the inner planar surface (17 in FIG. 1) of the blade, the second section 95 forms a bow-shaped protruberance as viewed from the side in FIG. 10.

FIG. 11 shows a tissue retractor 87 of the invention in the form of a dural retractor for retracting a dural sack 97 in the spinal canal of a patient undergoing spinal surgery. The second section 95 of the dural retractor engages the dural sack as shown and can be manipulated by means of an exposed knob (99 in FIGS. 9 and 10) which is used to slide the dural retractor upwardly and downwardly within the elongate passageway 91 provided in the elongate body portion of the retractor blade 93. The dural retractor moves the dural sacks to one side during surgery to thereby widen the field of view for the surgeon.

An invention has been provided with several advantages. The improved retractor blade of the invention provides a minimally invasive system which will eliminate many of the limiting factors of the presently existing instruments on the market. The retractor blade system of the invention provides improved visual and physical access by the surgeon to the surgical field. In the case of spinal surgery, the improved retractor blade system of the invention provides for safe and effective disc space preparation and implant insertion while minimizing trauma to tissue surrounding the surgical site. Both the surgeon preferring direct visualization by looking down the surgical portal, or the surgeon who prefers indirect visualization with a scope can use the improved system of the invention. The present system offers superior lighting and visualization when compared to the systems presently on the market. The improved lighting and visualization is created by incorporation of the light, the scope, and a suction device into a single retractor blade. These features eliminate cords and cannulas form the portal visual site, thereby increasing the area in the visual field. The resulting larger visual field increases the surgeon's ability to identify anatomy and operate with correct surgical orientation. Placement of the light source in the retraction blade allows light to be focused only in the surgical site. The attendant glare which was present in the past using older devices caused when over head lights or a head light beam hits a shiny retractor is eliminated. Since the light source is very close to the surgical site, small amounts of light energy will be required for a powerful lighting effect. The light source can be powered by a simple battery pack also incorporated into the blade design. Placement of the light source in the blade allows lower wattage lighting, which is safer for the patient, avoiding the possibility of burns to the patient's tissue.

The four blade system of the invention allows the ability to place space between the blades, which allows variable angles of instrument access through the portal. The four independent blades easily allow the width of this portal to be adjusted by the surgeon according to the needs required for the surgical procedure. The system of the invention also allows a surgeon to quickly convert the surgical procedure from a minimally invasive case to an open case by simply changing the position of the blades. It is not necessary to remove the minimally invasive access apparatus and replace it with open system retractors.

While the invention has been shown in only one of its forms, it is not thus limited but is susceptible to various changes and modifications without departing from the spirit thereof.

I claim:

1. A minimally invasive surgical exposure system, comprising: a support frame having opposing horizontally oriented sides, the sides being arranged to lie in a common plane generally perpendicular to one another in use, at least selected ones of the sides of the support frame being provided with holding fixtures for engaging a retractor blade; at least one retractor blade having a fastening element which is engageable with a selected holding fixture of the support frame, the at least one retractor blade having a substantially elongate, planar body portion having a length which extends in a plane generally perpendicular to the plane of the support frame when in use; the planar body portion of the retractor blade defining within the blade at least one visualization channel including an upper extent and a lower extent, the visualization channel enclosed within the blade from the upper extent to the lower extent, the lower extent being located proximate a site within a surgical portal when in use; a light source being incorporated integrally with the blade, the light source being located in communication with the visualization channel for illuminating the site; and wherein a power source is also incorporated integrally with the blade for powering the light source.

2. The system of claim 1, wherein the planar body portion of the retractor blade further defines within the blade a separate elongate utility channel enclosed within the blade, the utility channel extending from an upper extent of the blade to a lower extent thereof, the utility channel housing a selectable utility device which is used during surgery.

3. The system of claim 2, wherein the selectable utility device is a suction device having an upper end and a lower end, the lower end being dispatchable from the blade lower extent into the surgical site, the suction lower end having incorporated therein a coiled wire which can be controlled through tension to allow desired placement into the surgical site.

4. The system of claim 1, wherein the support frame is a four sided, substantially square member having an open interior space which is adjustable for engaging patient tissue and for spreading open an incision in said tissue in substantially a first plane, to create a surgical portal and wherein at least selected sides of the support frame are mechanically coupled together by a gear system for adjusting the interior space between the sides of the support frame.

5. The system of claim 1, wherein the elongate body portion of the retractor blade also houses a tissue retractor, the tissue retractor having a first section coplanar with the elongate body portion of the blade and a second section angularly oriented with respect to the first section for engaging tissue within a surgical site, the tissue retractor is slidably received within an elongate passage substantially centrally formed in the elongate body portion of the blade.

6. The system of claim 5, wherein the tissue retractor comprises a dural retractor for retracting a dural sack in a spinal canal of a patient undergoing spinal surgery.

7. A minimally invasive surgical exposure system, comprising: a support frame having two opposing pairs of horizontally oriented sides, the pairs of sides being arranged to lie in a common plane generally perpendicular to one another in use, each of the sides of the support frame being provide with a holding fixture for engaging a retractor blade; a set of four retractor blades, each retractor blade having a fastening element which is engageable with one of the holding fixtures of the support frame, each of the retractor blades having a substantially elongate, planar body portion having a length which extends in a plane generally perpendicular to the plane of the support frame when in use; the planar body portion of at least a selected one of the retractor blades having incorporated therein at least one visualization channel including an upper extent and a lower extent, the visualization channel enclosed within the blade from the upper extent to the lower extent, the lower extent being located proximate a site within a surgical portal; wherein a light source is located in communication with the visualization channel for illuminating the site; and wherein a power source is also incorporated integrally with the selected blade for powering the light source.

8. The system of claim 7, wherein the planar body portion of the selected retractor blade further defines within the blade a separate elongate utility channel, the utility channel enclosed within the blade and extending from an upper extent of the blade to a lower extent thereof, the utility channel housing a selectable utility device which is used during surgery.

9. The system of claim 8, wherein the selectable utility device is a suction device having an upper end and a lower end, the lower end being dispatchable from the blade lower extent into the surgical site, the suction lower end having incorporated therein a coiled wire which can be controlled through tension to allow desired placement into the surgical site.

10. The system of claim 7, wherein the support frame is a four sided, substantially square member having an open interior space which is adjustable for engaging patient tissue and for spreading open an incision in said tissue in substantially a first plane, to create a surgical portal and wherein at least selected sides of the support frame are mechanically coupled together by a gear system for adjusting the interior space between the sides of the support frame.

11. The system of claim 7, wherein the elongate body portion of the retractor blade also houses a tissue retractor, the tissue retractor having a first section coplanar with the elongate body portion of the blade and a second section angularly oriented with respect to the first section for engaging tissue within a surgical site, the tissue retractor being slidably received within an elongate passage substantially centrally formed in the elongate body portion of the blade.

12. The system of claim 11, wherein the tissue retractor comprises a dural retractor for retracting a dural sack in a spinal canal of a patient undergoing spinal surgery.

13. A minimally invasive surgical exposure system, comprising:

a support frame having opposing horizontally oriented sides, the sides being arranged to lie in a common plane generally perpendicular to one another in use, at least selected ones of the sides of the support frame being provided with holding fixtures for engaging a retractor blade;

at least one retractor blade having a fastening element which is engageable with a selected holding fixture of the support frame, the at least one retractor blade having a substantially elongate, planar body portion having a length which extends in a plane generally perpendicular to the plane of the support frame when in use;

the planar body portion of the retractor blade defining within the blade at least one visualization channel including an upper extent and a lower extent, the visualization channel enclosed within the blade from the upper extent to the lower extent, the lower extent being located proximate a site within a surgical portal when in use; and a light source being incorporated integrally with the blade, the light source being located in communication with the visualization channel for illuminating the site.

14. The system of claim 13, further comprising a power source incorporated integrally with the blade for powering the light source.

15. The system of claim 13 wherein the planar body portion of the retractor blade further defines within the blade a separate elongate utility channel enclosed within the blade, the utility channel extending from an upper extent of the blade to a lower extent thereof, the utility channel housing a selectable utility device which is used during surgery.

* * * * *